United States Patent
Weidl et al.

(10) Patent No.: US 10,327,705 B2
(45) Date of Patent: Jun. 25, 2019

(54) METHOD AND DEVICE TO MONITOR AT LEAST ONE VEHICLE PASSENGER AND METHOD TO CONTROL AT LEAST ONE ASSISTANCE DEVICE

(75) Inventors: Galia Weidl, Boeblingen (DE); Michael Schrauf, Esslingen (DE)

(73) Assignee: Daimler AG, Stuttgart (DE)

( * ) Notice: Subject to any disclaimer, the term of this patent is extended or adjusted under 35 U.S.C. 154(b) by 731 days.

(21) Appl. No.: 14/235,907

(22) PCT Filed: Jul. 24, 2012

(86) PCT No.: PCT/EP2012/003107
§ 371 (c)(1), (2), (4) Date: Jan. 29, 2014

(87) PCT Pub. No.: WO2013/020648
PCT Pub. Date: Feb. 14, 2013

(65) Prior Publication Data
US 2014/0135598 A1    May 15, 2014

(30) Foreign Application Priority Data

Aug. 5, 2011   (DE) .................. 10 2011 109 564

(51) Int. Cl.
*A61B 5/00* (2006.01)
*A61B 5/0205* (2006.01)
(Continued)

(52) U.S. Cl.
CPC .......... *A61B 5/6893* (2013.01); *A61B 5/0205* (2013.01); *A61B 5/18* (2013.01);
(Continued)

(58) Field of Classification Search
CPC ..... A61B 5/18; A61B 5/6893; A61B 5/02405; A61B 5/0064; A61B 5/02416;
(Continued)

(56) References Cited

U.S. PATENT DOCUMENTS

| 5,465,079 A * | 11/1995 | Bouchard | ............. | G01S 13/325 |
| | | | | 180/272 |
| 6,599,243 B2 * | 7/2003 | Woltermann | .......... | A61B 5/165 |
| | | | | 340/425.5 |

(Continued)

FOREIGN PATENT DOCUMENTS

| DE | 10 2007 046 037 B3 | 4/2009 |
| DE | 10 2009 016 936 A1 | 11/2009 |

(Continued)

OTHER PUBLICATIONS

International Search Report (PCT/ISA/210) with English translation dated Nov. 13, 2012 (Seven (7) pages).
(Continued)

*Primary Examiner* — Eugene T Wu
(74) *Attorney, Agent, or Firm* — Crowell & Moring LLP (57) ABSTRACT

A method for monitoring a vehicle passenger involves determining a current vital parameter value of at least one vital parameter of the vehicle passenger and, if necessary, a current environmental parameter value of at least one environmental parameter of an outer environmental of the vehicle. Depending upon the determined values, assistance can be provided to the vehicle passenger.

10 Claims, 4 Drawing Sheets

(51) Int. Cl.
| | | |
|---|---|---|
| *A61B 5/18* | (2006.01) | |
| *B60K 28/06* | (2006.01) | |
| *B60W 40/08* | (2012.01) | |
| *G16H 40/63* | (2018.01) | |
| *G16H 50/20* | (2018.01) | |
| *A61B 5/021* | (2006.01) | |
| *A61B 5/024* | (2006.01) | |
| *A61B 5/08* | (2006.01) | |
| *A61B 5/1455* | (2006.01) | |

(52) U.S. Cl.
CPC ............... *A61B 5/48* (2013.01); *B60K 28/06* (2013.01); *B60W 40/08* (2013.01); *G16H 40/63* (2018.01); *G16H 50/20* (2018.01); *A61B 5/0077* (2013.01); *A61B 5/021* (2013.01); *A61B 5/02405* (2013.01); *A61B 5/0816* (2013.01); *A61B 5/14551* (2013.01); *A61B 2560/0242* (2013.01); *B60W 2040/0818* (2013.01); *B60W 2420/42* (2013.01); *B60W 2530/14* (2013.01); *B60W 2540/22* (2013.01); *B60W 2550/00* (2013.01)

(58) Field of Classification Search
CPC . A61B 5/02444; A61B 5/1455; A61B 5/1176; A61B 5/7275; A61B 5/7282
See application file for complete search history.

(56) References Cited

U.S. PATENT DOCUMENTS

| | | | | |
|---|---|---|---|---|
| 6,957,142 | B2* | 10/2005 | Entenmann | G07C 5/085 701/117 |
| 7,027,621 | B1* | 4/2006 | Prokoski | G06K 9/00255 180/272 |
| 7,565,230 | B2 | 7/2009 | Gardner et al. | |
| 7,609,150 | B2* | 10/2009 | Wheatley | B60Q 9/008 340/436 |
| 2003/0146841 | A1* | 8/2003 | Koenig | A61B 5/18 340/576 |
| 2004/0088095 | A1* | 5/2004 | Eberle | B60K 28/02 701/45 |
| 2007/0182529 | A1* | 8/2007 | Dobler | B60K 28/06 340/438 |
| 2010/0009326 | A1 | 1/2010 | Mori | |
| 2011/0213511 | A1* | 9/2011 | Visconti | B60W 40/09 701/1 |
| 2012/0123644 | A1* | 5/2012 | Waldmann | B60T 7/042 701/45 |

FOREIGN PATENT DOCUMENTS

| | | |
|---|---|---|
| DE | 10 2009 053 407 A1 | 6/2010 |
| EP | 1 182 089 B2 | 2/2008 |
| EP | 2 340 976 A1 | 7/2011 |

OTHER PUBLICATIONS

German-language Written Opinion (PCT/ISA/237) dated Nov. 13, 2012 (Eight (8) pages).
German-language Office Action dated Apr. 30, 2012 (Eleven (11) pages).
Poh, et al., "Non-contact, automated cardiac pulse measurements using video imaging and blind source separation", Optics Express, May 7, 2010, No. 18, pp. 10762-10774, (Fourteen (14) pages).

* cited by examiner

METHOD AND DEVICE TO MONITOR AT LEAST ONE VEHICLE PASSENGER AND METHOD TO CONTROL AT LEAST ONE ASSISTANCE DEVICE

BACKGROUND AND SUMMARY OF THE INVENTION

Exemplary embodiments of the present invention relate to a method and device for monitoring at least one vehicle passenger, as well as a method to control at least one assistance device.

German patent document DE 10 2009 053 407 A1 disclose a method for the continuous monitoring of the medical state of a vehicle passenger, in particular the vehicle driver in which at least one physiological signal of a physiological parameter of the vehicle passenger, a vehicle parameter and/or an environmental parameter are continuously detected, determined or analyzed. The physiological parameter of the vehicle passenger is issued continuously by means of an output unit at the side of the vehicle passenger, in particular continuously displayed on the instrument panel of the vehicle.

European patent document EP 1 182 089 B2 discloses a method for warning a driver of a vehicle in which a critical situation is detected by vehicle sensors. Furthermore, an alertness level of the driver is determined, wherein an image of the driver is captured by a camera device and the image is processed by a computing unit. An alertness level of the driver is determined from the image, wherein a line of vision of the driver is determined by the computing unit. In the case of a determined high alertness level of the driver, the issuing of the warning is dispensed with. In the case of several warnings to be issued at the same time, a first warning of a critical situation, which lies in the line of vision of the driver, is only issued after a second warning of a critical situation, which lies outside of the line of vision of the driver.

German patent document DE 10 2009 016 936 A1 assigned to the assignee of the present application, the complete content of which is hereby incorporated by reference, discloses a driver assistance system to support a driver of a vehicle in the case of fatigue. The driving assistance system comprises a drowsiness detection system to detect fatigue of the driver. In the case of fatigue of the driver recognized by means of the drowsiness detection system, a flashing warning light of the vehicle is activated to warn other road users.

Furthermore, in the article by Ming-Zher Poh, Daniel J. McDuff, and Rosalind W. Picard, "Noncontact, automated cardiac pulse measurements using video imagine and blind source separation," Opt. Express 18, 10762-10774 (2010), the complete content of which is hereby incorporated by reference, discloses a method in which essentially the heart rate of the people is determined by means video sequences, captured by low-resolution video cameras under normal lighting conditions, of faces of people. The differences in brightness of the light reflected by the skin is measured and analyzed. First, the positions of the faces in the visual field of the camera are identified, then the video image in this section is broken up into red, green and blue portions and analyzed. During a heart beat the blood vessels—above all the arteries—expand slightly, as the pressure increases. This expansion causes an increase of the optical absorption and therefore also a decrease in the intensity of the light that is reflected by the face.

Exemplary embodiments of the present invention are directed to an improved method and device for monitoring at least one vehicle passenger in a vehicle and an improved method for controlling at least one assistance device of a vehicle.

In a method for monitoring at least one vehicle passenger in a vehicle, a current vital parameter value of at least one vital parameter of the vehicle passenger and, if necessary, a current environmental parameter value of at least one environmental parameter of an outer environment of the vehicle, are determined.

According to the invention, the vehicle passenger is identified and the current vital parameter value of the vehicle passenger is stored, if necessary together with the current environmental parameter value, and is compared to at least one older vital parameter value of the vehicle passenger, which has already been recorded and was recorded, if necessary, together with an older environmental parameter value, which corresponds to the current environmental parameter value. This means the current vital parameter value of the respective, clearly identified passenger is compared with one or several older vital parameter values of this vehicle passenger, if necessary with reference to the environmental context, wherein a short-term or long-term analysis of the vital state of the respective vehicle passenger is enabled by recording the vital parameter values. The comparison of the development of vital parameters over time comprises short-term, medium-term and longer-term changes. An analysis of progression over time of the vital parameter or a plurality of such vital parameters and furthermore preferably also parameters determined in another way, such as for example an alertness level, a line of vision, unconcentrated behavior, restlessness, fatigue and/or a stress level of the vehicle passenger, in particular of a respective vehicle driver, is enabled, if necessary with reference to the environmental context. This enables a vital state of the vehicle passenger, for example of a vehicle driver of the vehicle, to be assessed and suitable measures to be initiated in the case of a determined deterioration of the vital state, for example to activate functions of an assistance device of the vehicle, in order to at least indicate a potential risk of accident or, if necessary, to prevent an accident, to request help and/or to increase comfort of the vehicle passenger(s), in order to improve the vital state. This means the assistance device can, for example, be adapted to a current vehicle passenger state or to features of the vehicle driver, wherein his features can be evaluated by means of a stress level or the emotional state of the vehicle driver.

The clear identification of the respective vehicle passenger, the vital parameter values of whom are detected respectively, can, for example, occur by means of facial recognition by analyzing at least one currently captured image of the respective vehicle passenger or by another possibility of identification, for example by a registration in the vehicle by means of a password, by means of a code, by taking a finger print or by means of voice recognition. This means, for example, the people are clearly identified and the respective determined vital parameter values are allocated to the respective person and are stored and analyzed with reference to the person, even if several people use the vehicle interchangeably.

The vital parameters and/or symptoms that are able to be determined from these are monitored automatically over short, medium and/or longer time intervals and their trend development is observed. To that end, it is already sufficient if the respective vehicle passenger only spends a few minutes per day in the vehicle respectively.

In particular, a current state, in particular a state of vitality of the vehicle passenger can be very well assessed by the analysis of the current vital parameter value with reference to the environmental context in comparison to older vital parameter values, as, for example, in the new environmental, a deterioration of vital parameter values is normal due to a higher stress level. However, if the current vital parameter value deviates very strongly from the older vital parameter value, which was detected with a similar environmental parameter value, i.e. in a comparable environment, for example during a daily journey to work, a daily journey home, to the supermarket or the gym, i.e. during frequently reoccurring activities, or which was determined with very similar environmental parameters, for example at a road type or crossing type that is known to the vehicle driver, then this indicates a deterioration of the vital state of the driver and/or health problems, which could lead to a possible emergency situation or which can be counteracted by means of the assistance device, for example with a suitable comfort function of the vehicle. Thus, for example, pain relief can be effected by means of a massage function in a vehicle seat. In order to counteract an increased stress level or fatigue of the vehicle driver, essential oils can be sprayed by means of the ventilation and/or air conditioning function of the vehicle, which can be invigorating, refreshing or calming. For example, lavender oil is calming, thyme is invigorating, jasmine oil is soothing, calming and up-lifting and orange and lemon oil are mood-lifting. Furthermore, a chronic illness profile of the vehicle passenger can be reacted to accordingly, which can be determined by determination of (a) vital parameter(s), for example high blood pressure, a viral infection or a chronic obstructive pulmonary disorder (COPD).

This means an holistic situation analysis of the vehicle passenger, of the vehicle and of the vehicle environment is possible by means of the method and information and/or warnings to the vehicle passenger are to be formed dynamically and adapted to the determined and analyzed vital parameters. Furthermore, the assistance device(s) can be adapted to a vital state of the vehicle driver, in order to optimize in this way a security and a comfort of the vehicle passengers.

As they are recorded and stored in the vehicle, the stored vital parameters or vital parameter values are furthermore also available in an emergency situation for medical care. They can, for example, be transferred together with an automatically initiated emergency call to a hospital or casualty center, such that quick and adequate help can be initiated. Furthermore, for example, a long-term electrocardiogram can be produced and analyzed by a long-term analysis of the stored vital parameters and in this way, for example, a cardiac arrhythmia, also referred to as an arrhythmia, can be recognized and the vehicle passenger can be warned. For example, a visit to the doctor can be recommended to him/her.

The environmental parameter values can, for example, be determined by means of one or several environmental parameter sensor units, for example by means of a unit to determine the position of the vehicle by means of a global satellite navigation system to determine position. In this way, the determined vital parameter values can be allocated to a respective vehicle position and thus to a respective vehicle environment. Furthermore, alternatively or additionally, this environmental parameter sensor unit or a further environmental parameter sensor unit can be formed as a device to determine the environment of the vehicle, which has, for example, a radar, lidar and/or ultrasound sensor system and/or one or several cameras, for example mono and/or stereo cameras. In particular, for example, streets and/or crossings are detected by means of such cameras, such that the vital parameter values, for example, can be allocated to a respective street or crossing type, a respective traffic situation or a motorway situation. Thus the vital parameter values which were determined in connection with similar driving situations or vehicle environments can be compared with one another accordingly, such that, for example, short-term deteriorations of the vital parameters are very quickly able to be determined and long-term changes are able to be determined through the long-term analysis and can be indicated to the vehicle passenger.

Advantageously, a pulse rate and/or a breathing rate and/or a breathing volume and/or a heart rate variability and/or a skin temperature and/or a pumping capacity of the heart and/or a blood pressure and/or an oxygen concentration in the blood of the vehicle passenger, also referred to as oxygen saturation, and/or autonomous bodily functions, in particular functions of an autonomous nervous system of the vehicle passenger and/or pain statuses of the vehicle passenger is determined as a current vital parameter value. The heart rate variability (HRV) is connected to the heart rate and the breathing, i.e. the breathing rate and the breathing volume, via respiratory sinus arrhythmia, which describes a fluctuation of the heart rate in the synchronization with the breathing, such that it able to be determined via the determined heart rate, breathing rate and the determined breathing volume. Additionally vital functions or vital parameters or health risks such as resilience, stress tolerance, a cardiovascular risk and further health risks, as well as positive and negative emotional states such as joy, stress or anger can be determined from the heart rate variability. For example, further diagnostic parameters are determined or recognized by means of the vital parameters, for example tachycardia, brachycardia and/or viral infections, by means of the heart rate variability, the breathing, i.e. the breathing rate and/or the breathing volume, and/or the skin temperature. The current vital state of the vehicle passenger can be sufficiently accurately assessed by means of these vital parameter values in order to be able to indicate, for example, an inattention of the vehicle passenger, for example of the vehicle driver, or a threatening or already occurring unconsciousness or severe health problems.

The current vital parameter value can, for example, be determined by means of a vital parameter sensor unit, which is arranged on a vehicle seat, on a seat belt or on a steering wheel or the vehicle. The sensor unit can be integrated into "smart textiles" in the vehicle or on the vehicle passenger.

For example, a plurality of such vital parameter sensor units for one or several vital parameters is also possible. In a particularly advantageous embodiment, the current vital parameter value, however, is determined, alternatively or additionally, by image analysis by means of at least one image of the vehicle passenger captured by an image capturing unit. This means the image capturing unit is the vital parameter sensor unit. In this way, the respective vehicle passenger, whose vital parameter values are determined, can also be clearly identified, for example by means of facial recognition, such that the determined vital parameter values can be clearly allocated to the respective vehicle passenger and can be stored and analyzed in the vehicle with reference to the person.

Therein, an image capturing unit that is already installed in the vehicle, for example in the region of a steering column or in the region of a visibly positioned telematic display, and is directed towards the vehicle passenger(s), preferably towards the vehicle driver, serves as an image capturing unit. Vital parameter values of several vital parameters of the respective vehicle passenger can also be detected simultaneously by means of this image capturing unit or all data can be detected simultaneously, from which the vital parameter values of the respective vehicle passengers can be determined by means of image analysis. Such image capturing units are installed in the vehicle, for example, to recognize alertness of the vehicle driver. Therein a video camera with low resolution, for example a so-called CCD camera, is already sufficient. Special lighting devices are also not required, as environmental lighting, for example daylight, is already sufficient. A robustness of a signal detection of the image capturing unit is clearly improved by partially redundant information, for example in a RGB color signal of the image capturing unit, and in particular by the possibility of the signal detection with a black and white camera for dark driving sections, i.e. for a dark environment, for example during a drive through a tunnel or at night. Therein, signal detection in the so-called HSC black and white signal occurs, if necessary by means of lighting by an infra-red light source. Therein, for example, a separate image capturing unit is not required, but the present image capturing unit is switched into a black and white mode. Advantageously, this occurs automatically depending on respective proportions of environmental light.

Preferably, the current vital parameter value is determined by detection of an optical absorption value and/or of an intensity value of reflected light of a skin region of the vehicle passenger and/or by a determination of a change of this optical absorption value and/or of this intensity value. During a heartbeat, blood vessels, in particular arteries, expand slightly, as pressure increases in the blood vessels. This expansion causes an increase of the optical absorption and therefore also a decrease of the intensity of the reflected light which is reflected by the skin region. By determining the differences in brightness of the light reflected by the skin region over time, vital parameter values, in particular the pulse rate, can be determined. This method is also called photoplethysmography. The foundations of the method are, for example, described in the article by Ming-Zher Poh, Daniel J. McDuff, and Rosalind W. Picard, "Noncontact, automated cardiac pulse measurements using video imaging and blind source separation," Opt. Express 18 10762-10774 (2010), the complete contents of which is hereby included herein by reference.

Preferably, at least one region suitable for image analysis is searched for in each of the images during the image processing and only this region is analyzed. This region is a region in the images in which a sufficiently large skin region of the vehicle passenger is displayed. Preferably, a region of the images is searched for and analyzed as a region that is suitable for image analysis, which contains the face of the vehicle passenger, as in this region a sufficiently larger skin region that is able to be analyzed is available and as, in particular, image capturing units that are already installed in the vehicle and which are used, for example, to recognize alertness, are directed towards the face of the vehicle passenger, in particular of the vehicle driver. Vital parameter values of one or several vital parameters of several vehicle passengers can also be detected simultaneously with the method, wherein the image regions are determined, in which the faces of the vehicle passengers are situated and are analyzed separately from one another.

Advantageously, color images are captured as images of the vehicle passengers, in particular so-called RGB images, wherein the region of the images suitable for image analysis is split into individual color channels and at least one color channel is analyzed to determine the current vital parameter value. For example, the region suitable for image analysis is divided into red, green and blue portions, i.e. color channels. Therein, preferably, the green portion or color channel is analyzed, as the accuracy of the obtained results is highest with this color channel.

The skin temperature, the oxygen concentration or oxygen saturation and the blood pressure of the vehicle passenger, for example, can be determined from a combination of the color channels, more precisely from a phase shift and/or a change in amplitude between the color channels or color signals.

Preferably, a spectral power density of the color channel of the region suitable for image analysis is determined by means of a fast Fourier transform. The differences in brightness of the light reflected by the skin region over time can then be determined by means of the determined spectral power density and the vital parameter value(s) can be determined therefrom.

The vital parameter values determined in this way can also be combined with values of the vehicle passengers determined in another way, in order to thus obtain a better overall image of the state of the vehicle passenger. In this way, for example, fatigue or inattention of the vehicle driver can be determined in good time and with a low error rate. Thus, for example, movements of the respective vehicle passenger, in particular of the vehicle driver, can be determined by sensors integrated into the vehicle seat or into the vehicle seat textiles, which can indicate unconcentrated behavior, restlessness, stress or the beginnings of fatigue. This can, for example, be combined with the determined pulse rate, in order to obtain a better estimate.

A device to monitor at least one vehicle passenger in a vehicle comprises at least one vital parameter sensor unit to determine a current vital parameter value of at least one vital parameter of the vehicle passenger and at least on environmental parameter sensor unit to determine at least one current environmental parameter value of at least one environmental parameter of an outer environment of the vehicle.

According to the invention, the vehicle passenger is able to be identified and the current vital parameter value of the vehicle passenger is able to be stored in a storage unit together with the current environmental parameter value. The current vital parameter value is able to be compared in an evaluation unit with at least one older vital parameter value of the vehicle passenger, which has already been stored and which is stored together with an older environmental parameter value in the storage unit, which corresponds to the current environmental parameter value.

This enables a vital state of the vehicle passenger, for example a vehicle driver of the vehicle to be assessed and suitable measures to be initiated in the case of a determined deterioration of the vital state, for example functions of an assistance device of the vehicle to be activated in order to at least indicate a potential risk of accident or if necessary to prevent an accident, to request help and/or to increase comfort of the vehicle passenger(s) in order to thus improve the vital state, as has already been described with regard to the method, which is able to be carried out by means of the device, to monitor at least one vehicle passenger in a vehicle.

The clear identification of the respective vehicle passenger, the vital parameter values of which are detected respectively, can, for example, occur by means of facial recognition by analyzing at least one currently captured image of the respective vehicle passenger or by another possibility of identification, for example by a registration in the vehicle by means of a password, by means of a code, by taking a finger print or by means of voice recognition. This means, for example, the people are clearly identified and the respective determined vital parameter values are allocated to the respective person and stored and analyzed with reference to the person, even if several people use the vehicle interchangeably.

The environmental parameter sensor unit is, for example, a unit to determine the position of the vehicle by means of a global satellite navigation system for determining position. Furthermore, alternatively or additionally, this environmental parameter sensor unit or a further environmental parameter sensor unit can be formed as a device to detect the environment of the vehicle, which has, for example, a radar, lidar and/or ultrasound sensor system and/or one or several cameras, for example mono and/or stereo cameras. In particular, for example, roads and/or crossings are able to be detected by means of such cameras, such that the vital parameter values, for example, are to be allocated to a respective road and or crossing type or a respective traffic situation, for example a motorway situation. Thus, the vital parameter values, which were determined in connection with similar driving situations or driving environments are able to be compared with one another accordingly, such that, for example, short-term deteriorations of the vital parameters are able to be determined very quickly and long-term changes are able to be determined by the long-term analysis and can be indicated to the vehicle passenger.

The current vital parameter value is able to be compared with one or several older vital parameter values by means of the device with reference to environmental context, wherein a short-term, medium-term or long-term analysis of the vital state of the respective vehicle passenger is enabled by storing the vital parameter values. This means an analysis of progression over time of the vital parameter or a plurality of such vital parameters with reference to environmental context and preferably, furthermore, also parameters determined in a different such as for example an alertness level, a line of vision, unconcentrated behavior, restlessness, fatigue and/or a stress level of the vehicle passenger, in particular of a vehicle driver, is enabled.

The vital parameters and/or symptoms that are able to be determined from these are automatically able to be monitored over a longer period of time and their trend development is able to be observed. Therein it is already sufficient if the respective vehicle passenger only spends a few minutes per day in the vehicle respectively.

In particular, through the analysis of the current vital parameter value with reference to environmental context in comparison to older vital parameter values, a current state, in particular vitality of the vehicle passenger is able to assessed very well, as, for example, a deterioration of vital parameter values is normal in a new environment due to an increased stress level. However, if the current vital parameter value differs very strongly from an older vital parameter value, which was determined with the same environmental parameter value, i.e. in a comparable environment, for example during a daily journey to work, a daily journey home, to the shops or to the gym, i.e. during frequently reoccurring activities, or which was determined with very similar environmental parameters, for example at a road type or crossing type that is known to the vehicle driver, then this indicates a deterioration of the vital state of the driver or a health problem, which could lead to a possible emergency situation or which can be counteracted by means of the assistance device, for example with a suitable comfort function of the vehicle. Thus, for example, pain relief can be effected by means of a massage function in a vehicle seat. In order to counteract an increased stress level or fatigue of the vehicle driver, essential oils can be sprayed by means of the ventilation and/or air conditioning function of the vehicle, which can be invigorating, refreshing or calming. For example, lavender oil is calming, thyme is invigorating, jasmine oil is soothing, calming and uplifting and orange and lemon oil are mood-lifting. Furthermore, a chronic illness profile of the vehicle passenger can be reacted to accordingly which can be determined by determination of (a) vital parameter(s), for example high blood pressure, a viral infection or a chronic obstructive pulmonary disorder (COPD).

This means that an holistic situation analysis of the vehicle passenger, of the vehicle and of the vehicle environment is possible by means of the device and of the method that is able to be carried out with this, and information and/or warnings to the vehicle passenger are to be formed dynamically and are to be adapted to the determined and analyzed vital parameter. Furthermore, the assistance device(s) can be adapted to a vital state of the vehicle driver, in order to optimize in this way the security and comfort of the vehicle passengers.

Furthermore, the stored vital parameters or vital parameter values are available, for example, in an emergency situation for medical care, as they are recorded and stored in the vehicle. They can, for example be transferred together with an automatically initiated emergency call to a hospital or casualty center, such that quick and adequate help can be initiated. Furthermore, for example, a long-term electrocardiogram can be produced and analyzed by a long-term analysis of the stored vital parameters and in this way, for example, a cardiac arrhythmia, also called an arrhythmia, can be recognized and the vehicle passenger can be warned. For example, a visit to the doctor can be recommended to him.

The vital parameter sensor unit is, for example, arranged on a vehicle seat, on a seat belt or on a steering wheel of the vehicle. For example, a plurality of such vital parameter sensor units for one or several vital parameters is also possible. However, in a particularly advantageous embodiment, the device comprises, alternatively or additionally, at least one image capturing unit to capture images of the vehicle passenger and an image processing unit, by means of which a vital parameter value of the vital parameter of the vehicle passenger is able to be determined by image analysis of the captured image, as has already been described with respect to the method able to be carried out by the device.

In a method to control at least one assistance device of a vehicle using the method to monitor at least one vehicle passenger, according to the invention, at least one function of the assistance device is activated, if a current vital parameter value of at least one vital parameter of a respective vehicle passenger deviates from a predetermined value or value region for this vital parameter and/or deviates from a stored older vital parameter value of the respective vehicle passenger, which was stored together with an older environmental parameter value, which corresponds to the current environmental parameter value. In this way, the assistance device can intervene in a supporting manner in the case of poor or deteriorating vital parameter values of the vehicle passenger(s), in particular of the vehicle driver, in order indicate, for example, a potential risk of accident or if necessary to prevent an accident, to request help and/or to increase comfort of the vehicle passengers(s) in order to thus improve the vital state. This can occur very accurately as the vital parameter values are compared to one another with reference to environmental context and as the danger of a false evaluation of vital parameter values is greatly reduced in this way. Thus, for example, the functions of the assistance device are not activated, if a deterioration of vital parameter values is to be ascribed to an increased stress level due to an unknown environment, or for example, comfort functions are targetedly activated in order to thus enable a relaxation of the vehicle passenger. If the determined current vital parameter values deteriorates however with respect to older vital parameter values, which were detected in a comparable environment, for example on a daily journey to work, then this indicates an acute health problem and/or a deterioration of the vital state of the driver, such that corresponding other functions of the assistance device are to be activated.

Preferably, an intervention in a steering device, a braking device and/or a drive train of the vehicle and/or an optical, aural and/or haptic warning device is activated as a function of the assistance device. In this way, the vehicle, as, for example, is described in DE 10 2009 016 936 A1, the complete content of which is hereby incorporated by reference, can be steered automatically to the edge of a road and brought to a standstill there by a corresponding intervention in the steering device, braking device and/or drive train of the vehicle. Particularly advantageously, the intervention in the steering device, braking device and/or in the drive train of the vehicle can occur in such a way that the vehicle is steered autonomously to the nearest emergency assistance establishment, for example to the casualty of the nearest hospital.

Alternatively or additionally, warning devices of the vehicle can be activated, for example outer warning devices in the form of flashing warning lights and/or a horn of the vehicle, in order to warn other road users, and/or warning devices within the vehicle can be activated, in order to warn the vehicle passenger(s), for example in order to wake a vehicle driver who has fallen asleep or to indicate to other vehicle passengers a poor or deteriorating vital state of the vehicle driver such that they can operate the steering wheel and/or the handbrake of the vehicle in order to brake the vehicle and/or to steer the vehicle to the edge of the road.

Alternatively or additionally, advantageously at least one comfort function and/or emergency call function is activated as a function of the assistance device. Vital parameter values of the vehicle passenger(s) can be improved through the activation of the comfort function or a plurality of such comfort functions, for example if the determined vital parameter value(s) indicate fatigue, in particular of the vehicle driver. A massage function of a vehicle seat, interior ventilation and/or an air conditioning function of the vehicle can then be activated, for example. Therein, for example, essential oils or another refreshing medium can be introduced into the interior of the vehicle to refresh the vehicle passengers. Furthermore, the relevant vehicle passenger can be indicated about his current vital situation by optical, aural or haptic means, preferably with a recommendation of suitable counter measures, for example to take a restorative break, to move regularly and/or to take on sufficient fluids. In this way, the vehicle passenger can also be reminded, for example, to take required medication. Furthermore, devices of the vehicle to support or calm the driver can be activated in a targeted manner, for example in the case of an increased stress level recognized by means of the vital parameters, for example a navigation device or audio equipment of the vehicle, i.e. for example a car radio.

Additionally, the vehicle passenger(s) can also be warned of threatening health risks, for example of threatening cardio-vascular problems. Therein it is particularly advantageous to determine the vital parameters of the vehicle passenger(s), for example of the vehicle driver, over longer periods of time, for example several days or weeks and to analyze their development, in particular with reference to environmental context, such that slow deterioration can also be determined. In particular in the case of older passengers and/or passengers whose health is at risk or affected, in particular vehicle drivers, their sense of security and well-being is greatly increased. Additionally, in a medical emergency an automatic emergency call can be made, wherein preferably the detected vital parameter value can be transferred to an emergency call center or a hospital, such that quick and adequate medical help can be given. For this purpose, current positional date of the vehicle is preferably determined and transferred with the emergency call.

BRIEF DESCRIPTION OF THE DRAWING FIGURES

Exemplary embodiments of the invention are illustrated in greater detail by means of drawings.

Here are shown.

Parts that correspond to one another have the same reference numerals added to them in all figures.

DETAILED DESCRIPTION

Figure 1:
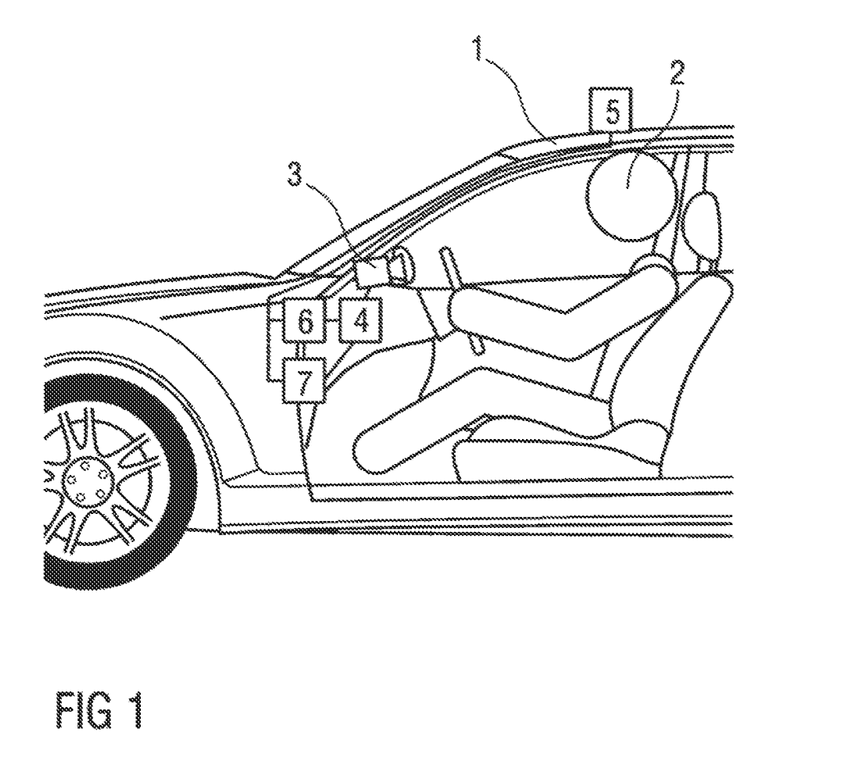
FIG. 1 a schematic depiction of a vehicle having a vehicle passenger and an image capturing unit directed towards him, FIG. 2 a schematic depiction of three color channels, FIG. 3 a detailed view of a region from FIG. 2, FIG. 4 a schematic depiction of coefficients of a detected color signal and FIG. 5 a schematic method procedure.

FIG. 1 shows a schematic depiction of a vehicle 1 with a vehicle passenger 2 and an image capturing unit 3 directed towards him as a device to monitor the vehicle passenger 2. In a method for monitoring the passenger 2, images of the vehicle passenger 2 are captured by means of the image capturing unit 3, which is a vital parameter sensor unit, for example in the form of a video sequence, and are analyzed by means of an image processing unit 4, in order to determine at least one current vital parameter value of the vehicle passenger 2, for example a pulse rate or heart rate and/or a breathing rate and/or a breathing volume. A heart frequency variability can be determined therefrom. The heart frequency variability, also referred to as the HRV, is connected to the heart rate and the breathing i.e. the breathing rate and the breathing volume, via the respiratory sinus arrhythmia, which describes a fluctuation of the heart rate in synchronization with the breathing. Additional vital functions or vital parameters or health risks such as resilience, stress tolerance, a cardiovascular risk and further health risks such as positive and negative emotional states such as joy, stress or anger can be detected from the heart frequency variability.

Furthermore, a skin temperature and/or pumping capacity, for example, of the heart and/or a blood pressure and/or an oxygen concentration in the blood of the vehicle passenger 2, also referred to as an oxygen saturation, and/or autonomous bodily functions, in particular functions of an autonomous nervous system of the vehicle passenger 2 and/or pain status of the vehicle passenger 2, can be determined. A vital state of the vehicle passenger 2 and a change of the vital state can be assessed by means of the determined vital parameter(s) of the vehicle passenger 2.

For example, further diagnostic parameters can be determined or recognized by means of the vital parameter values, for example tachycardia, brachycardia and/or viral infections, by means of the heart frequency variability, the breathing, i.e. the breathing rate and/or the breathing volume and/or the skin temperature. An assessment of the current vital state of the vehicle passenger 2 can be optimized by means of these further vital parameters, such that, if necessary, for example, inattention of the vehicle passenger 2, for example of the vehicle driver, or a threatening or already occurring unconsciousness or severe health problems can be indicated.

The image capturing unit 3 is preferably an image capturing unit 3 that is already installed in the vehicle 1, for example, as is depicted here, in the region of the steering wheel or in the region of a visibly positioned telematic display, and is directed towards the vehicle passenger 2, in the example depicted here towards the vehicle driver. Therein, a video camera with low resolution is sufficient to carry out the monitoring method, for example a so-called CCD camera. Special lighting devices are also not required, but a normal environmental lighting in the vehicle 1, for example daylight, is already sufficient. The current vital parameter values of the vehicle passenger 2 are detected simultaneously by means of this image capturing unit 3 or all data is detected simultaneously, from which the current vital parameter values of the vehicle passenger 2 can be determined by means of an image analysis.

A robustness of a signal detection of the image capturing unit 3 is clearly improved by partially redundant information, for example in an RGB color signal of the image capturing unit 3 and in particular by a possibility of the signal detection with a black and white camera for dark driving sections, i.e. for a dark environment, for example during a drive through a tunnel or at night. Therein, signal detection in the so-called HSB black and white signal occurs, if necessary by means of lighting by an infra-red light source. Therein, for example, a separate image detection unit 3 is not required, but the present image detection unit 3 is switched to a black and white mode. Advantageously, this occurs automatically depending on respective proportions of environmental light.

The at least one vital parameter value or the vital parameter values are determined by a detection of an optical absorption value and/or an intensity value of reflected light of a skin region of the vehicle passenger 2 and/or a determination of a change of this optical absorption value and/or this intensity value. During a heartbeat, blood vessels, in particular arteries, expand slightly, as pressure increases in the blood vessels. This expansion causes an increase of the optical absorption and therefore as a decrease in the intensity of reflected light which is reflected by the skin region. Vital parameters of the vehicle passenger 2, in particular the pulse rate or heart rate and preferably also the breathing rate and the breathing volume can be determined by the detection of the differences in brightness of the light reflected by the skin region over time. This method is also called photoplethysmography. The foundations of the method are, for example, described in the article by Ming-Zher Poh, Daniel J. McDuff, and Rosalind W. Picard, "Noncontact, automated cardiac pulse measurements using video imaging and blind source separation," Opt. Express 18 10762-10774 (2010), the complete contents of which is hereby incorporated by reference.

During the image processing, at least one region suitable for image analysis is searched for in each of the images by means of suitable methods and only this region is analyzed. This region is a region in the images, in which a sufficiently large skin region of the vehicle passenger 2 is displayed. Preferably a region of the images is searched for and analyzed as a region suitable for image analysis which contains the face of the vehicle passenger 2, as a sufficiently large skin region which is able to be analyzed is available in this region and as, in particular, image detection units 3 which are already installed in the vehicle 1 and which for example are used to recognize alertness, as is also in the example depicted here, are directed towards the face of the vehicle passenger 2 in particular of the vehicle driver.

The location of such regions suitable for image analysis is possible, for example, by means of methods for facial recognition in images. One or several of the vital parameters of several vehicle passengers 2 can also be determined simultaneously with the method if several vehicle passengers 2 are detected by the image capturing unit 3, wherein the image regions are determined in which the faces of the vehicle passengers 2 are located and are analyzed separately from one another. Furthermore, in this way the respective vehicle passenger 2 can be identified clearly by means of the facial recognition function, such that the determined vital parameter values can be clearly allocated to the respective passenger 2. Thus, for example, even if several people use the vehicle 1 interchangeably, the people can be clearly identified and the respectively determined vital parameter values of the respective person can be stored and allocated with respect to the person.

Figure 2:
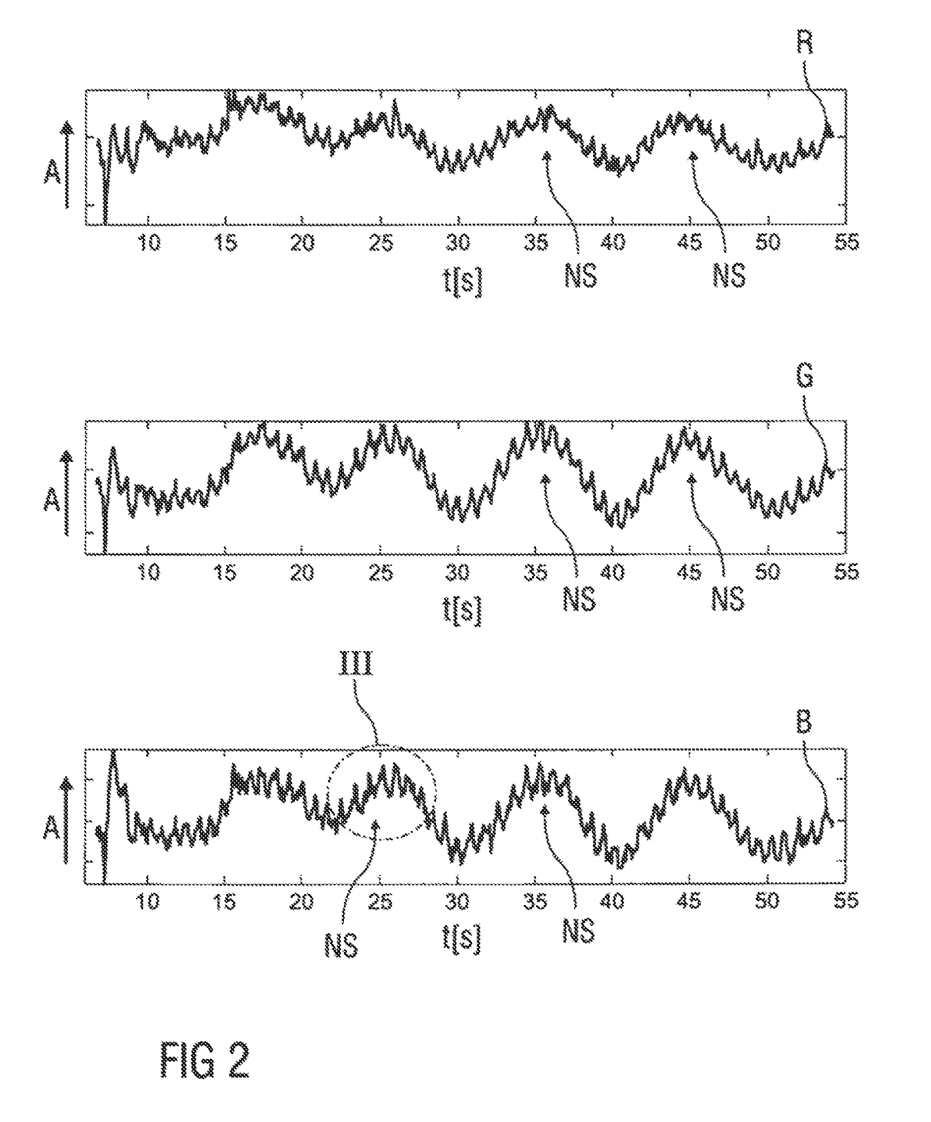

Advantageously, color images are captured as images of the vehicle passenger 2, in particular so-called RGB images, wherein the region of the images suitable for image analysis is split into individual color portions or color channels, in the case of RGB images into the corresponding RGB color channels, i.e. into a red color channel R, a green color channel G and blue color channel B, as is depicted in FIG. 2, and at least one color channel RGB is analyzed to determine the at least one vital parameter. Therein, preferably, in particular, the green portion or color channel, i.e. the green color channel G, is analyzed, as in the case of this channel, the accuracy of the obtained result is the highest. In FIG. 2, these progressions of the color channels RGB are depicted over the time t.

Figure 3:
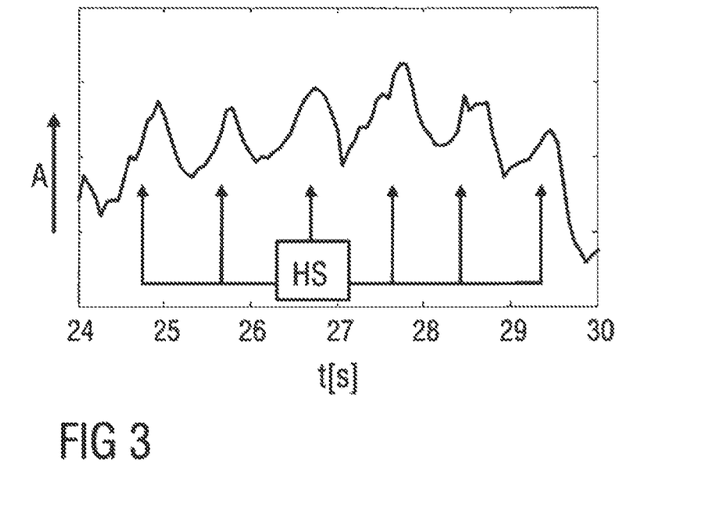

The breathing rate is determined through the analysis of the low-frequency vibrations NS of the color signal or color channels RGB, the breathing volume is determined through the analysis of the amplitudes A of the low-frequency vibrations NS and the heart rate is determined by the analysis of the high-frequency vibrations HS. In FIG. 3, the high-frequency vibrations HS of an individual low-frequency vibration of a color channel RGB is depicted.

A spectral power density of the color channel RGB to be analyzed of the region suitable for image analysis is determined by means of a fast Fourier transform. The differences in brightness of the light reflected by the skin region over time, and from this the vital parameter(s) of the vehicle passenger(s) 2 can then be determined by means of the determined spectral power density.

Figure 4:
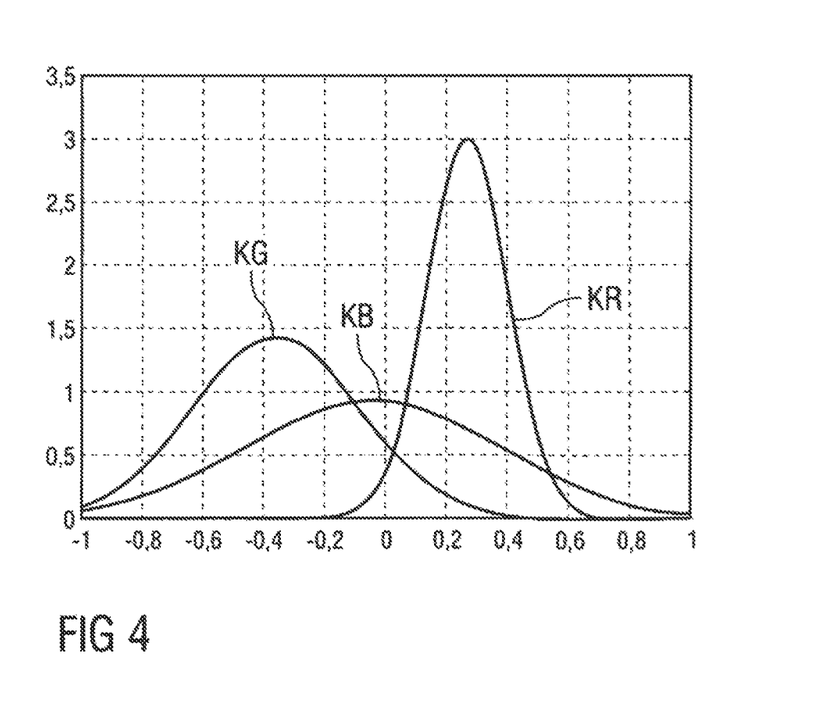

In FIG. 4, coefficients KR, KG, KB of the color signal split into the three color channels RGB of an area of skin of the vehicle passenger 2, for example of their face, is depicted. The skin temperature, the blood pressure and the oxygen saturation of the blood of the vehicle passenger 2 can be determined from the phase shift and/or the amplitude change between the coefficients KR, KG, KB of the RGB color signal.

The method is very simple and cost-effective to implement and carry out in the vehicle 1 due to the image capturing unit 3, which only has to have a low resolution, as well as due to the implementation under normal environmental lighting conditions, i.e. without additional special light sources. Additionally, the method is very robust with respect to different skin colors as well as with respect to movements of the vehicle passenger(s) 2 during the image capturing. The determination of the current vital parameter values is therein sufficiently exact in order to be able to determine sufficiently exactly the vital state of the vehicle passenger(s) 2 as well as a change of the vital state by means of the determined vital parameter value(s), such that a vital state, which indicates for example an acute emergency situation and requires medical help or which for example could have effects on the safe driving of the vehicle 1, is able to be recognized with high certainty.

Furthermore, in order to be able to assess such changes of the vital parameter values indicating illness, emergency states or loss of comfort even better, a current environmental parameter value of at least one environmental parameter is determined by means of an environmental parameter sensor unit 5. This can, for example, be a current position of the vehicle 1, which is determined by means of a global satellite navigation system to determine position. Alternatively or additionally, a road and/or crossing type can be determined for example, at which the vehicle 1 is currently situated. For this purpose, the environmental parameter sensor unit 5 or a further environmental parameter sensor unit is formed as a radar, lidar and/or ultrasound sensor system and/or one or several cameras, for example mono and/or stereo cameras and/or C2X communication. C2X is an abbreviation for "Car to X" or "Car to Car". The "X" can also not only represent another car, but also a transport-relevant infrastructure unit. The corresponding environmentally-relevant data is consolidated, the corresponding development of the traffic situation, also including the other road users, is cognitively analyzed and the risk is evaluated depending on the vital state, the alertness or the distraction or fatigue of the driver.

This enables an analysis of the determined vital parameter values with reference to context in the context of the vehicle environment. This means the determined current vital parameter values can be compared in this way with older vital parameter values, which have already been stored and which were determined at an early point in time at the same position or which were determined in a similar environment, for example in a similar driving situation, for example on a motorway. Furthermore, in the analysis of the vital parameter values with reference to context, it can be included whether the vehicle driver is situated in a traffic situation that is known to him, for example on a daily journey to work, home, to the shops or to the gym, or in an unfamiliar traffic situation that is new for him, whereby his vital parameter values change, for example due to an increased stress level. It is thus, for example, able to be determined in a simple way, whether deteriorated vital parameter values are to be ascribed to an acute emergency situation or to an environmental parameter that is new for the vehicle passenger 2. Functions of an assistance device are to be activated accordingly and varyingly. In an acute emergency situation, for example, an emergency call is to be activated and the vehicle 1 for example to be steered autonomously in order, for example, to be brought to a stop safely by a targeted intervention in a braking system, a steering system and/or drive train. In the case of vital parameter values that are only deteriorating due to an unfamiliar situation, stress-reducing functions of the assistance device are to be activated, for example a massage function in the vehicle seat, audio equipment of the vehicle 2 in order to play relaxing music or an air-conditioning or ventilation function of the vehicle 1, by means of which, for example, essential oils can be sprayed.

Furthermore, a long-term assessment of the vital and health state of the respective vehicle passenger 2 is possible via the long-term analysis of the stored vital parameter values of the vehicle passenger 2.

In order to enable this analysis of the vital parameter values with reference to environmental context, the currently determined vital parameter value is stored in the storage unit 6 together with the currently determined environmental parameter value. Furthermore, the current vital parameter value is compared in an evaluation unit 7 with at least one older vital parameter value of the vehicle passenger 2 which has already been stored and which is stored in the storage unit 6 together with the older environmental parameter value, which corresponds to the current environmental parameter value.

This means the current vital parameter value is compared to one or several older vital parameter values, wherein the short-term, medium-term and/or long-term analysis of the vital state of the respective vehicle passenger 2 is enabled by storing the vital parameter values. This means an analysis of progression over time of the vital parameter or a plurality of such vital parameters with reference to the environmental context and preferably, furthermore, also parameters determined in a different ways, such as for example an alertness level, distraction, a line of vision, unconcentrated behavior, restlessness, fatigue and/or a stress level of the vehicle passenger 2, in particular of a vehicle driver, is enabled.

The vital parameters and/or symptoms determined from these are automatically monitored over a longer period of time and their trend development is observed. Therein it is already sufficient if the respective vehicle passenger 2 only spends a few minutes per day in the vehicle 1 respectively.

In particular, a current state, in particular the vitality of the vehicle passenger 2, can be very well assessed by the analysis of the current vital parameter value with reference to environmental context in comparison to older vital parameter values, as, for example, a deterioration of vital parameter values is normal in a new environment due to a higher stress level. However, if the current vital parameter value deviates very strongly from an older vital parameter value, which was determined with a similar environmental parameter value, i.e. in a comparable environment, for example during a daily journey to work, a daily journey home, to the shops or to the gym, i.e. during frequently reoccurring activities, or which were determined with very similar environmental parameters, for example at a road type or a crossing type known to the vehicle driver, then this indicates a health problem, which could lead to a possible emergency situation or which can be counteracted by means of the assistance device, for example, such as has already been described, with a suitable comfort function of the vehicle 1. Thus, for example, a pain reduction can be effected by means of a massage function in a vehicle seat. In order to counteract an increased stress level or a fatigue of the vehicle driver, essential oils can be sprayed, for example by means of a ventilation and/or air-conditioning function of the vehicle 1, which is invigorating, refreshing or calming. For example, lavender oil is calming, thyme is invigorating, jasmine oil is soothing, calming and uplifting and orange and lemon oil are mood-lifting. Furthermore a chronic illness profile of the vehicle passenger 2 can be reacted to accordingly, which can be determined by the determination of the vital parameter(s), for example high blood pressure, a viral infection or a chronic obstructive pulmonary disorder (COPD).

This means a holistic situation analysis of the vehicle passenger 2, of the vehicle 1 and of the vehicle environment is possible by means of the method and information and/or warnings to the vehicle passenger 2 are to be dynamically designed and adapted to the determined and analyzed vital parameters. Furthermore, the assistance device(s) can be adapted to a vital state of the vehicle driver in order to optimize in this way a security and a comfort of the vehicle passengers 2.

Furthermore the stored vital parameters or vital parameter values are also available in an emergency situation for medical care, as they are recorded and stored in the vehicle 1. They can, for example, be transferred together with an automatically initiated emergency call to a hospital or casualty center, such that quick and adequate help can be initiated Furthermore, a long-term electrocardiogram can be produced and analyzed, for example, by a long-term analysis of the stored vital parameters, and in this way for example a cardiac arrhythmia, also called an arrhythmia, is recognized and the vehicle passenger 2 is warned. For example, a visit to the doctor can be recommended to him.

The monitoring method or the vital parameter(s) of the vehicle passenger 2, in particular the vehicle driver, determined in this way, can, as has already been indicated, be used in a method to control at least one assistance device of the vehicle 1. Therein, at least one function of the assistance device is activated, if a current vital parameter value of at least one vital parameter deviates from a predetermined value or value region for this vital parameter and/or deviates from a stored older vital parameter value, which was stored together with an older environmental parameter value, which corresponds to the current environmental parameter value.

In this way, the assistance device can intervene in a supporting manner in the case of poor or deteriorating vital parameters of the vehicle passenger(s) 2 in particular of the vehicle driver, in order, for example, to prevent an accident, to request help and/or to increase the comfort of the vehicle passenger(s) 2 in order to thus improve the vital state. This means the assistance device can, for example, be adapted to the current vehicle driver state or to the features of the vehicle driver, wherein his features for example can be evaluated by means of a stress level of the vehicle driver.

Preferably, an intervention in a steering device, a braking device and/or in a drive train of the vehicle 1 and/or an optical, aural and/or haptic warning device is activated as a function of the assistance device. In this way, the vehicle 1, as is described for example in DE 10 2009 016 936 A1, the complete content of which is hereby incorporated by reference, is steered to a roadside automatically and brought to a standstill there by a corresponding intervention in the steering device, braking device and/or the drive train of the vehicle 1. Particularly advantageously, the intervention in the steering device, the braking device and/or in the drive train of the vehicle 1 can occur in such a way that the vehicle 1 is autonomously steered to the next emergency assistance establishment, for example to a casualty of the nearest hospital.

Alternatively or additionally, warning devices of the vehicle 1 can be activated, for example outer warning devices in the form of a flashing warning light and/or a horn of the vehicle 1 in order to warn other road users, and/or warning devices in the vehicle interior can be activated in order to warn the vehicle passenger(s), for example in order to wake a sleeping vehicle driver or to indicate to other vehicle passengers 2 a deteriorating vital parameter of the vehicle driver, which possibly indicates a deteriorated health state, such that they can for example operate the steering wheel and/or the hand brake of the vehicle 1 or this can be actuated autonomously by actuators in order to brake the vehicle 1 and/or to steer it to the roadside.

Advantageously, at least one comfort function and/or emergency call function is activated, alternatively or additionally, as a function of the assistance device. Through the activation of the comfort function or a plurality of such comfort functions, vital parameters of the vehicle passenger(s) 2 can be improved, for example if the detected vital parameter(s) indicate a fatigue, in particular of the vehicle driver.

Then, for example, a massage function of a vehicle seat, interior ventilation and/or an air-conditioning function of the vehicle 1 can be activated. Therein, for example, essential oils or another refreshing medium can be introduced into an interior of the vehicle 1 to refresh the vehicle passenger(s) 2. Furthermore, the current vital situation of the relevant passenger 2 can be indicated to him through optical, aural and/or haptic means, preferably accompanied by a recommendation of a suitable countermeasure, for example to take a restorative break, to move around regularly and/or to take on sufficient fluids. In this way, the vehicle passenger 2 can also be reminded to take required medication. Furthermore, for example, devices of the vehicle 1 that support and/or calm the vehicle driver can be activated in the case of an increased stress level recognized by means of the vital parameters, for example a navigation device or audio equipment of the vehicle 1 i.e. for example the car radio.

Additionally, the vehicle passengers 2 can also be warned of threatening health risks, for example of threatening cardiovascular problems. Therein it is particularly advantageous to determine the vital parameters of the vehicle passenger(s) 2 for example of the vehicle driver, over longer periods of time, for example several days or weeks, and to analyze their progression, such that slow deteriorations can also be determined. In particular, in the case of older passengers 2 and/or passengers 2 who are at risk or affected in terms of health, in particular vehicle drivers, their sense of security and well-being is thus considerably improved. Additionally, in a medical emergency, an automatic emergency call can be made, wherein preferably the detected and stored vital parameters are transferred to an emergency call center or to a hospital such that quick and adequate medical help can be given. For this purpose, current positional data of the vehicle 1 is also preferably determined and transferred with the emergency call.

The vital parameters determined by means of the monitoring method can also be combined with values of the vehicle passenger(s) 2 determined in other ways, in order to obtain a better overall image of a state of the vehicle passenger(s) 2. In this way, for example, fatigue or inattention of the vehicle driver can be determined in good time and with a low error rate. Thus, for example, movements of the respective vehicle passenger 2, in particular of the vehicle driver, can be determined by sensors in the vehicle seat or in the vehicle textiles, which can indicate unconcentrated behavior, restlessness, stress or the beginnings of fatigue. Additionally, the inattention recognition function, for which the image capturing unit 3 is originally installed in the vehicle 1, can also be used. In this way, determined additional values of the vehicle passenger(s) 2 can for example be combined with the determined pulse rate and/or with other determined vital parameter values in order to obtain a better estimation of the vital state of the vehicle passenger(s) 2.

Figure 5:
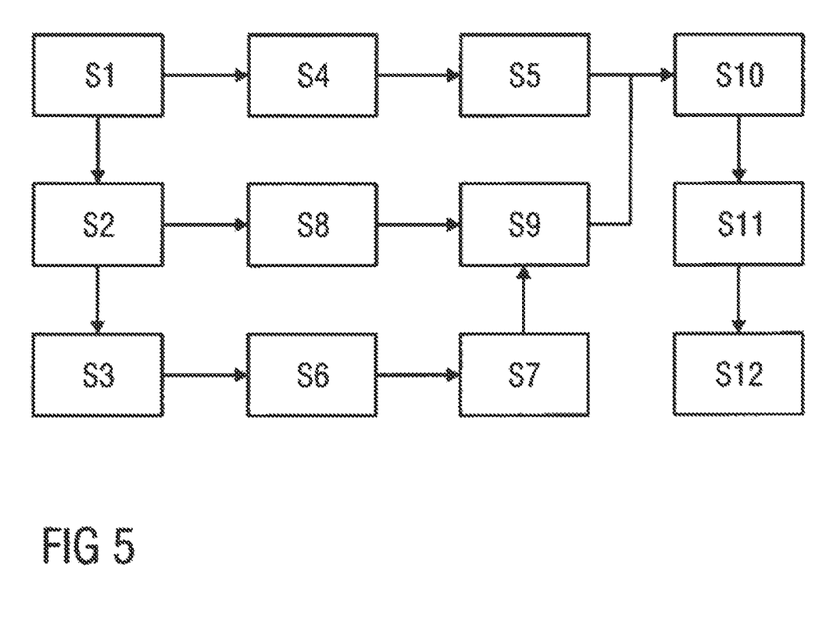

In FIG. 5, a method procedure of the method to control at least one assistance device of the vehicle 1 using the method to monitor the vehicle passenger 2 in the vehicle 1 is once again schematically depicted, wherein the image capturing unit 3 is used as a vital parameter sensor unit. Therein the order in the method procedure is not set by a numbering in the following listed method steps. Several method steps can also be carried out at the same time for example, or some of the method steps can also be carried out in a different order. In a first method step S1, images of the vehicle passenger 2, in particular of the vehicle driver, are captured by means of the image capturing unit 3. In a second method step S2, the vehicle passenger 2 is clearly identified via his face, such that in a third method step S3, a comparison of determined current vital parameter values with older vital parameter values of the vehicle passenger 2 that have already been stored is enables and in a fourth method step S4 an allocation of environmental parameter values to this vehicle passenger 2 is enabled as a basis for comparison with reference to context. In a fifth method step S5, the current environmental parameter values are determined by means of the environmental parameter sensor unit 5, for example the position of the vehicle 1 is determined by means of the global satellite navigation system for determination of position, wherein it can be determined whether the driver is situated in an environment that is known to him, for example on a journey to work, home, to the shops or to the gym. Furthermore, a situation analysis is able to be determined by means of global consolidation of detected environmental data and a traffic situation is, in which the vehicle driver is situated, able to be determined by corresponding cameras, for example a crossing type or a road type or a motorway, such that a level of familiarity of the environment for the vehicle driver is able to be determined.

The global consolidation of the environmental data contains environmental parameters that are determined with cameras and/or with radar and/or with lidar and/or ultrasound sensor systems and/or one or several cameras, for example mono and/or stereo cameras and/or C2X (car-to-car and car-to-infrastructure) communication. This consolidated environmentally detected data is analyzed with cognitive methods in order to evaluate the corresponding development of the traffic situation, including the behavior of the other road users, and to recognize and try to prevent possible risks depending on the vital state, the alertness or the distraction or the fatigue of the driver.

In a sixth method step S6, an image processing of the images captured of the vehicle passenger 2 by means of the image capturing unit 3 is carried out, such that the current vital parameter values can be determined in a seventh method step S7. Furthermore, in an eighth method step S8, for example, further parameters are determined by an image analysis of the individual images captured by means of the image capturing unit 3, for example a level of alertness, a line of vision, a level of fatigue as well as unconcentrated behavior and/or restlessness and/or a stress level of the vehicle passenger 2. In a ninth method step S9, the determined vital parameter values and the determined further parameters are summarized into passenger-relevant data. In a tenth method step S10, an analysis of this passenger-relevant data with reference to environmental context occurs using the environmental parameter values, such that a state recognition of the vehicle passenger 2 and furthermore a short-term, medium-term and/or long-term monitoring of the vital parameters of the vehicle passenger 2 over time with reference to environmental context is enabled. This analysis occurs in an eleventh method step S11, such that in a twelfth method step S12, the already described functions of the assistance device can be activated according to the analyzed vital parameter values.

The following embodiments are conceivable in combination with all of the methods and devices described up to this point:

A more robust and timely analysis with a lower error rate when recognizing the driver state can be provided by the trend analysis with reference to environmental context in combination with the vital parameters that are camera-based in particular and/or with the same or similar camera-based driver observing device to determine driver states. Determined driver states are typically alertness, distraction, fatigue. Integrated sensors can also be used on the driver's seat, seat belt, steering wheel to detect these or sensors integrated into "smart textiles" to recognize movement patterns, from which unconcentrated behavior, restlessness, stress or the beginnings of fatigue can be indicated, and/or vital parameters of the vehicle passenger.

Further information with diagnostic value can be determined from the data, in particular the vital parameters, for example regarding abnormal health states of the vehicle passenger. Or a chronic illness profile of the vehicle passengers is produced, for example high blood pressure, heart arrhythmia, a viral infection and/or a chronic obstructive pulmonary disorder (COPD). Furthermore, trend developments of the vital state can be recognized or changes of the chronic illness profile on a short-term, medium-term and/or long-term time scale.

The current vital state of the vehicle passenger can be assessed by means of the measured vital parameters, such that for example inattention of the vehicle driver or a threatening or already occurring unconsciousness or severe health problems can better be indicated from further information.

A suitable device can additionally comprise a control display screen, e.g. a display of a telematic system or an individual display directed towards the front close to the visual field of the driver or a head-up display, such that at least one warning or reminder function of the assistance device can be well depicted.

A device according to the invention comprises at least one warning or reminder function in the form of an optical, aural and/or haptic means, which indicates the current vital situation, preferably accompanied by a recommendation of suitable countermeasures, for example to take a restorative break, to move regularly and/or to take on sufficient fluids and/or a reminder to take required medication.

A device according to the invention can also comprise at least one function, which autonomously activates the supporting and/or calming measures and which adapts to the individual vital state of the driver and/or to the environmental context. For example, comfort functions such as massage in the vehicle seat and/or spraying of essential oils from the air-conditioning and/or ventilation system of the vehicle and/or suitable media or music adapted to the situation from audio equipment of the vehicle can be provided in the vehicle.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A method for monitoring at least one vehicle passenger in a vehicle, the method comprising:
   determining, by a first sensor unit, a current vital parameter value of at least one vital parameter of the vehicle passenger;
   detecting, by a second sensor unit, a current environmental parameter value of at least one environmental parameter of an outer environment of the vehicle;
   storing the current vital parameter value of the vehicle passenger together with the current environmental parameter value;
   identifying the vehicle passenger;
   comparing the current vital parameter value of the vehicle passenger with at least one older, previously stored vital parameter value of the same vehicle passenger, wherein the older vital parameter value is previously stored together with an older environmental parameter value, which corresponds to the current environmental parameter value; and
   determining a health condition of the vehicle passenger by the comparing.

2. A method according to claim 1, wherein the determined current vital parameter value is one of a pulse rate, a breathing rate, a breathing volume, a heart rate variability, a skin temperature, a pumping capacity of the heart, a blood pressure, an oxygen concentration in the blood of the vehicle passenger, autonomous bodily functions of the vehicle passenger, or pain states of the vehicle passenger.

3. The method according to claim 1, wherein the first sensor unit is at least one image capturing unit and the current vital parameter value is determined by image analysis of at least one image of the vehicle passenger captured by the at least one image capturing unit.

4. The method according to claim 3, wherein the current vital parameter value is determined by a detection of an optical absorption value, by an intensity value of reflected light of a skin region of the vehicle passenger, or by a determination of a change of the optical absorption value or of the intensity value.

5. The method according to claim 3, wherein, during the image processing, at least one region suitable for image analysis in each of the images is searched for and only this region is analyzed.

6. The method according to claim 5, wherein color pictures are captured as images of the vehicle passenger, wherein the region of the images suitable for image analysis is split into individual color channels and at least one color channel is analyzed to determine the current vital parameter value.

7. The method according to claim 1, further comprising:
   activating at least one function of an assistance device of the vehicle if the current vital parameter value of at least one vital parameter of a respective vehicle passenger deviates from a predetermined value or value region for the at least one vital parameter or deviates from a stored older vital parameter value of the vehicle passenger, which was stored together with an older environmental parameter value corresponding to the current environmental parameter value.

8. The method according to claim 1, further comprising:
   activating, as a function of an assistance device of the vehicle and based on the determining of the health condition, an intervention in a steering device, braking device, a drive train of the vehicle, an optical warning device, an aural warning device, haptic warning device, at least one comfort function, or an emergency call function.

9. A device to monitor at least one vehicle passenger in a vehicle, comprising:
   at least one vital parameter sensor unit configured to determine a current vital parameter value of at least one vital parameter of the vehicle passenger;
   at least one environmental parameter sensor unit configured to determine at least one current environmental parameters value of at least on environmental parameter of an outer environmental of the vehicle;
   a storage unit that is configured to store
      an identification of the vehicle passenger along with the current vital parameter value of the vehicle passenger and the at least one environmental parameter value, and
      at least one older vital parameter value of the vehicle passenger along with an older environmental parameter value, which corresponds to the current environmental parameter value,
   an evaluation unit configured to compare the current vital parameter value with the at least one older vital parameter value of the vehicle passenger to determine a health condition of the vehicle passenger.

10. The device according to claim 9, further comprising:
    at least one image capturing unit configured to capture images of the vehicle passenger,
    wherein the at least one vital parameter sensor unit is an image processing unit configured to determine the current vital parameter value of the vital parameter of the vehicle passenger by image analysis of the captured images.

* * * * *